US008066664B2

(12) United States Patent
LaDuca et al.

(10) Patent No.: US 8,066,664 B2
(45) Date of Patent: Nov. 29, 2011

(54) TRI-DIRECTIONAL ARTICULATING CATHETER

(75) Inventors: Robert C. LaDuca, Santa Cruz, CA (US); Paul A. LaDuca, Buffalo, CA (US)

(73) Assignee: Taheri LaDuca LLC, Santa Cruz, CA (US)

(*) Notice: Subject to any disclaimer, the term of this patent is extended or adjusted under 35 U.S.C. 154(b) by 987 days.

(21) Appl. No.: 11/638,246

(22) Filed: Dec. 12, 2006

(65) Prior Publication Data
US 2007/0276324 A1   Nov. 29, 2007

Related U.S. Application Data

(60) Provisional application No. 60/749,731, filed on Dec. 12, 2005.

(51) Int. Cl.
*A61M 31/00* (2006.01)
(52) U.S. Cl. ................................. 604/95.04
(58) Field of Classification Search ............ 604/95.04, 604/103.07
See application file for complete search history.

(56) References Cited

U.S. PATENT DOCUMENTS

| | | | | |
|---|---|---|---|---|
| 5,322,064 A | * | 6/1994 | Lundquist | 600/381 |
| 5,507,725 A | * | 4/1996 | Savage et al. | 604/95.04 |
| 5,656,030 A | | 8/1997 | Hunjan et al. | |
| 6,500,167 B1 | * | 12/2002 | Webster, Jr. | 604/528 |
| 6,533,783 B1 | * | 3/2003 | Tollner | 606/49 |
| 6,652,506 B2 | * | 11/2003 | Bowe et al. | 604/523 |
| 6,716,207 B2 | * | 4/2004 | Farnholtz | 604/523 |
| 6,783,510 B1 | * | 8/2004 | Gibson et al. | 604/95.01 |
| 7,056,314 B1 | * | 6/2006 | Florio et al. | 604/528 |
| 7,187,963 B2 | * | 3/2007 | Coleman et al. | 600/374 |
| 7,374,553 B2 | * | 5/2008 | Koerner et al. | 604/95.04 |
| 7,691,095 B2 | * | 4/2010 | Bednarek et al. | 604/523 |
| 2005/0277875 A1 | * | 12/2005 | Selkee | 604/95.04 |
| 2009/0157066 A1 | * | 6/2009 | Satake | 606/27 |

OTHER PUBLICATIONS

Khargi et al., "Surgical Treatment of atrial fibrillation: a ic review," *Eur. J. Cardiothorac. Surg.*, 27(2):258-65, Feb. 2005.

* cited by examiner

*Primary Examiner* — Nicholas D Lucchesi
*Assistant Examiner* — Diva Ranade
(74) *Attorney, Agent, or Firm* — Levine Bagade Han LLP

(57) ABSTRACT

A catheter capable of articulating in two and three directions is provided. Articulation at the distal tip of the catheter is facilitated by applying selective tension on a steering wire disposed in a lumen that resides peripheral to a central working lumen. Tension on the steering wire through the peripheral lumen causes the catheter tip to bend while the central working lumen resists compression.

11 Claims, 4 Drawing Sheets

TRI-DIRECTIONAL ARTICULATING CATHETER

CROSS-REFERENCE TO RELATED APPLICATIONS

This application claims the benefit of U.S. Provisional Application No. 60/749,731 filed Dec. 12, 2005 which is incorporated herein by reference in its entirety.

FIELD

The present invention relates generally to the field of steerable catheters having the ability to articulate in two or three directions.

BACKGROUND OF THE INVENTION

With the popularity of minimally invasive medical procedures, catheter designers continue to revise and improve catheters for medical use, trying to build catheters that can articulate in mammalian subjects and perform the challenging functions demanded of minimally invasive procedures. Catheters for minimally invasive procedures need to bend at the distal tip and need to allow access through the catheter-body by instruments that perform the procedure. Catheters with steerable wires and proximal controls have been built and described. The challenge continues with these catheters to build a device that can better articulate to a site in the mammal and once at that site to position the tip properly for the procedure. The catheters also need to steer easily and to hold an articulated position once the correct angle of catheter bend is achieved. Along these lines, problems have continued in determining optimal place merits of the steering wires in the catheter. The goal is to convey the most effective tension to the distal tip through the steering wire, see e.g. U.S. Pat. No. 5,507,725 which describes placement of the steering wires in the catheter wall.

Another problem has been how to steer the wires so that the practitioner can position the catheter and still be able to control instruments that access the catheter to perform the procedure, see e.g. U.S. Pat. No. 5,656,030 for a description of a catheter with a complicated steering control mechanism. Catheters that articulate in a single direction using a pull wire have been described, see e.g. U.S. Pat. No. 6,783,510, but this catheter lacks the usefulness of a catheter that can articulate in more than one direction.

Particularly for performing catheter-based procedures at the heart, or other procedures where it is advantageous to have a steerable catheter, it would be desirable to have a catheter with a distal tip that can articulate in more than one direction in order to adjust the positioning of the catheter to the contours of the site, and a catheter that can be controlled easily, and accurately, while still providing the opportunity for instrument access through a central working lumen. The present invention overcomes some of the deficiencies in the current catheter art by providing the following invention.

SUMMARY OF THE INVENTION

Figures 1A, 1B, 1C:
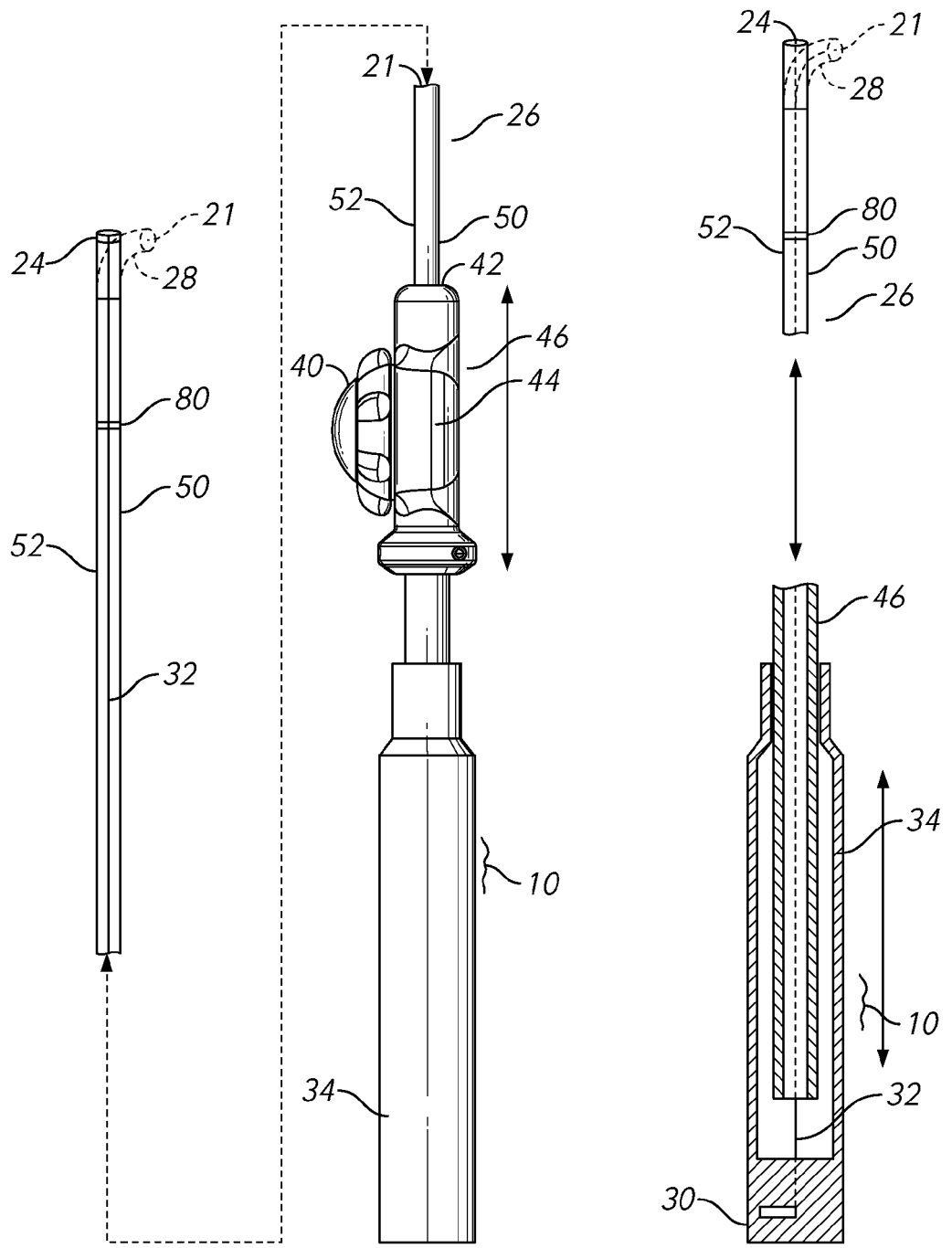
FIG. 1 depicts an elongate catheter body having the ability to perform tri-directional steering and articulation of the distal tip of the catheter.

The invention is a catheter with a central working lumen that provides bi- and tri-directional articulation at the distal tip while also being capable of resisting compression of the central working lumen. The central working lumen may thus be accessed during the procedure by one or more instruments because it has not compressed. The instruments are needed to perform particular given functions that support the procedure as a whole. A risk of compression in the central working lumen occurs when selective tension is applied on steering wires that are attached to the distal tip of the catheter. The tension facilitates the distal tip articulation but also risks compression of the central lumen. In the invention, the distal tip of the catheter remains flexible enough to bend in response to selective tension placed on the steering wires and at the same time the central lumen resists compression due to the gradually increased strength of the elongate catheter body as it moves proximally from the distal tip. In other words, the catheter is designed to be most flexible at the tip, and as you move proximally from the tip, the flexibility of the catheter decreases, while the wall strength increases. Accordingly, the distal tip is able to respond to steering signals that bend the tip without causing the central working lumen to compress.

An aspect of the invention that contributes to the quality of the catheter to resist compression is that the steering wires are placed in lumens disposed on an exterior surface of the central working lumen. The configuration of the peripheral lumens allows selective tension to be applied to the steering wire so that the tip bends but the central lumen does not compress.

In addition to peripheral lumens that hold the steering wires for steering the catheter tip, the catheter can have multiple additional peripheral lumens disposed on the exterior surface of the central working lumen in order to provide access to various other instruments involved in a procedure, instruments that do not require access through the central working lumen. Such instruments might include, for example, instruments that infuse fluid or gas, aspiration instruments, instruments that provide suction or light, scopes, cameras, and other various instruments that perform adjunctive work in a given procedure. Generally, during the catheter use, key functioning instruments will access the central working lumen, for example, for delivery of an item to the site (e.g. a pacemaker lead delivery device), delivery of a therapeutic agent to the site (e.g. delivery of a therapeutic fluid or emulsion), or instruments with suction to provide stabilization of the catheter tip at the wall of the target organ.

A donut balloon embodiment to these catheters facilitates fluid occlusion in a lumen with fluid flow while a procedure is underway. The donut balloon also provides access through one or more peripheral lumens to the site through the balloon, thereby avoiding direct contact with tissue or blood where such contact is not necessary or beneficial to the function of the accessing instruments.

The catheters of the invention are well-suited to procedures involving the heart organ and vascular lumens, or other procedures at other target organs in mammals as well.

Methods of using the catheters so described for various medical procedures are also provided, as is a method of making the catheters.

DETAILED DESCRIPTION OF THE INVENTION

One embodiment of the invention is a catheter having an elongate catheter body configured so that the distal tip can articulate in two opposite directions along a plane of articulation without compression of the central working lumen. The articulation is accomplished by steering two wires that are placed within opposed peripheral lumens that themselves are disposed on an exterior surface of a central working lumen. The positioning of the opposed peripheral lumens creates the plane of articulation. The placement of the steering wires in peripheral lumens exterior to the central working lumen provides resistance to compression at the distal tip along the length of a bend that occurs when selective tension is applied to one wire.

The material that constitutes the distal tip is composed of combinations of materials in order to provide maximum flexibility at the very tip and increasing strength (and so reduced flexibility and reduced tendency for compression) in the material as it moves proximally along the elongate catheter body. The placement of the steering wires in peripheral lumens provides the opportunity to create a catheter that bends but which central working lumen resists compression because the wires pull in separate lumens external to the central working lumen and as such allow the central working lumen to remain open.

The steering wires of the catheter with bidirectional articulation are both attached at the distal tip. The attachment can be by any functional means, including, for example, a ring at the distal tip to which the wires are soldered, or that the wires are embedded in the composite plastic or polymer material at the tip. Wires embedded in a composite of plastic or polymer can be coiled at the attachment place, particularly in a reverse coil, to provide a strong attachment that won't pull out of the composite material when selective tension is applied to the wire. To steer the wires selective tension is applied to one wire at a time and the wire is pulled from a position on the proximal end of the catheter. Tension on a single wire results in an articulation in a single direction within the plane of articulation defined by the positions of the peripheral lumens that hold the wires. Applying selective tension to the second wire by pulling it results in an articulation in a second opposite direction. The proximal steering means for these wires can be as simple as a torquer attached at the wire at the proximal end of the catheter, so that when the torquer of one steering wire is pulled the distal tip articulates in one direction, and when the torquer of the other steering wire is pulled the distal tip articulates on the other, opposite direction.

A rather more sophisticated means for applying selective tension to the steering wires resides in an embodiment comprising a rotatable steering unit and its rotatable steering knob for steering the distal tip in a direction within the plane of articulation. The steering unit is located at the proximal end of the catheter, outside the mammalian subject so that it can be steered by the operator. The first and second steering wires attach to the rotatable steering knob on opposite sides of the knob, the two attachment points being radially opposed to one another. When the steering knob is turned clockwise, one wire receives selective tension and the distal tip of the catheter articulates in one direction in the plane of articulation defined by the positions of the peripheral lumens opposite each other. When the steering knob is turned counterclockwise, the other wire receives selective tension and the distal tip of the catheter articulates in an opposite direction, however, still in the plane of articulation. The steering knob has an internal chamber with radially opposed circumferential tracks each comprising a pin attached to an internal surface of the rotatable member. The pins are slidable within their respective tracks. The first and second wires each attach to one of the pins. Thus, when the steering knob is turned clockwise, the pin moves in the track and applies selective tension to the attached wire. The selective tension on the wire pulls the wire at its distal attachment, and the tip of the catheter bends in a direction in the plane of articulation. The opposite direction is articulated in the same way with a turn of the knob counterclockwise.

The means for applying selective tension to the steering wires can itself also comprise a locking mechanism so that when the practitioner does not desire to make the catheter tip articulate one way or the other, the steering knob can be locked and the wires will remain in place. Once the practitioner desires to facilitate articulation at the catheter tip, the locking mechanism is released and the knob is then free to rotate clockwise or counterclockwise with the coordinate effects on the attached steering wires. Once a wire has been pulled sufficiently to create the desired articulation, angle, bend or configuration at the tip, the knob position can then be locked into place to hold the distal tip position while the procedure is conducted. The locking mechanism can be any locking mechanism that will work under the circumstances, for example a cog that holds the steering knob in place, and when the knob is raised off the cog, e.g. by use of a spring, the knob can turn. Additionally, release of the lock position can allow for an adjustment of the configuration or bend of the catheter tip. Thereafter, the operator can re-lock the steering knob so that friction can be maintained on the steering wire experiencing the selective tension, and the procedure can continue. Adjustable friction is thus maintained at the steering knob so that the selected optimal tip deflection is maintained during the procedure.

Sometimes during minimally invasive surgical procedures there is a need for the catheter tip to latch-on to the organ wall to perform the procedure. An example of this is when pacemaker leads are delivered to the heart muscle. One way to achieve the proper localization of the catheter tip at the organ wall is to apply suction through the central working lumen and articulate the catheter to just the right angle at the organ wall. The suction when applied then affixes the catheter tip at the wall for the lead delivery. The suction is released and the catheter removed when the lead placement is complete.

In order to provide tri-articulation, the bidirectional catheter can further comprise a third wire for articulating the distal tip of the catheter at an angle outside the plane of articulation of the first two wires. This is accomplished by providing a third steering wire and disposing it in its own peripheral lumen running from an attachment at the distal tip within the peripheral lumen along the elongate catheter to the proximal end of the catheter where it is attached to a means for providing selective tension on the wire. The attachment means at the distal tip can be a ring to which the wire is attached, the ring being affixed or embedded in the composite material (e.g. a plastic or polymer) at the distal tip. Alternatively, the wire can be wound in a coil (particularly a reverse coil that will tend to distribute the selective tension down the wire rather than receive it at a single point where the wire attaches) and the coil is embedded in the composite material at the distal tip of the catheter.

The means for applying selective tension on the third steering wire as with the first two steering wires can be as simple as a torquer attached to the proximal end of the wire as it hangs outside the peripheral lumen at the proximal most end of the catheter body. Alternatively, the means for applying selective tension on the third steering wire can be, for example, a tube residing over the proximal end of the elongate catheter to which the proximal end of the third steering wire is attached. The tube is slidable over the elongate catheter, particularly in a proximal direction, so that with the third wire attached and the tube is slid proximally, selective tension is placed on the third wire and the distal tip of the catheter bends in response to this tension. The bend resulting from selective tension on the third wire is at an angle outside the plane of articulation of the first two steering wires, and as with all the articulation angles of the catheter can be at an angle greater than 90 degrees. The angle determination can be made depending on the needs of the procedure.

With both the two-wire and the three-wire embodiments of the invention, a key feature is that the distal tip is flexible, so that it will bend in response to selective tension placed on the steering wires, and that it resists compression so that the central working lumen does not compress when the catheter bends. These two features can be accomplished by a number of means including, but not limited to using a braided wire mixed with a composite plastic or polymer material that is formed to harden around the wire. The braid angle of the wire is tight and small at the tip of the catheter and gradually, as one moves along the catheter length proximally, the braid angle gets larger, which increases the strength (and non-compressibility) of the catheter body. The braid angle change can be noted as a shift in 10 per inch crosses (PIC count) of the wires of the braid, so that at the very tip where it is needed to have the catheter most flexible, the PIC count are greater, and as the elongate catheter moves proximally the PIC count decreases.

Another way to make the elongate catheter flexible at the tip and non-compressible where it bends is to provide a gradual diameter shift in the central working lumen which is narrow at the tip. The diameter of the central lumen then gradually increases as the elongate catheter runs proximally. The smaller diameter at the distal tip provides maximum flexibility at the tip, and as the diameter of the central working lumen increases, so does the strength of the catheter body and its non-compressibility. Yet another way to provide gradual increase in non-compressibility (and decrease in flexibility) running in the distal to proximal direction along the catheter is to increase the durometer of the composite plastic or polymer material as you move proximally. The durometer of the material can be increased by means that are standard in the art for doing so. Lastly, a metal coil can be covered with a metal mesh braid and then embedded in the composite plastic or polymer which will increase both the flexibility of the structure and the non-compressibility of the central lumen as the length moves proximally.

An additional feature of the invention is that it can have multiple peripheral lumens, in addition to any of the three steering wire peripheral lumens already provided, and all these peripheral lumens are disposed on an exterior surface of the central working lumen. These additional peripheral lumens provide the opportunity for additional instrument access to a working site within the mammalian subject once the catheter is positioned at the site. Instruments that are useful for various purposes in the procedure may be placed in the peripheral lumens for accessing the site to perform a specific function. For example, instruments for visualization, e.g. a scope, camera, light or other visualization aid may be placed in peripheral lumens. Also, instruments' that infuse or remove fluids or gases can be placed in peripheral lumens, e.g. saline, contrast agent, or gas can be infused by instruments in peripheral lumens. Coordinately, suction can be applied from an instrument in a peripheral lumen, e.g. to clear the site of fluid or tissue while working.

In addition to providing access to some instruments, the peripheral lumens can carry the steering wires, as with the embodiments of the invention that provide for 1, 2 or 3 steering wires to which selective tension can be applied to bend the distal tip of the catheter. The peripheral lumens are important for the steering wire disposition because the peripheral lumens provide the ability to put selective tension on a steering wire disposed within a peripheral lumen at an attachment at the tip and with that tension provide a bend in the catheter as a whole, without a compression of the central working lumen.

An additional embodiment of the catheter invention includes a donut-shaped balloon at the distal tip of the catheter. The donut shaped balloon is affixed on the exterior of the peripheral lumens that themselves reside circumferentially on the exterior of the central working lumen. The inside edge of the donut-shaped balloon is affixed to the interior wall of the central working lumen. Thus, the balloon can be inflated and when inflated will encase the distal exits of the peripheral lumens, while forming an expanded circumferential border around the central working lumen. The donut balloon provides a means for instruments that access the site through a peripheral lumen to reside at the site without contacting fluids or tissue. The balloon configuration is useful for instruments such as visualization instruments that can do their work through the wall of the balloon and don't need to actually contact material at the site to perform their function. The balloon configuration also assists the catheter function when accessing a lumen that carries fluid, providing occlusion of fluid flow by inflation of the balloon, i.e. in situations where vascular occlusion is desirable.

Turning now to the features of the device depicted in the figures, FIG. 1 depicts a side view of the catheter 10 in two portions, distal and proximal. FIG. 1A represents the distal portion. FIG. 1B represents the proximal portion. FIG. 1C presents a longitudinal cross section of catheter 10 to show the central 32 steering wire and first steering wire 50 and second steering wire 52 locations. FIG. 1A depicts the distal end of the catheter 10, having an elongate body 26 with a central working lumen 21 therein disposed. The catheter has attachment position at ring 80 for steering wire 50 and steering wire 52 to attach at the distal end, and tip attachment 24 for attaching wire 32. Tip 28 is shown with a hypothetical articulation in dotted lines. Steering wires 50 and 52 for control of a first and second directional articulation in the same plane of articulation are disposed in the elongate catheter body 26 and run from attachment 80 to the proximal end having the steering unit 44, where the steering wires 50 and 52 are attached inside the steering unit 44. Steering wire 32 for articulation of the tip of the catheter outside the plane of articulation defined by the location of peripheral lumens holding steering wires 50 and 52 is attached at attachment 24 and this wire runs along the elongate catheter body 26 to a proximal location 30 where it is attached. Slidable unit 34 contains the attachment 30 and pulls on the steering wire 32 when it slides proximally away from the tip causing an angular bend at the catheter tip 28 outside the plane of articulation that steering wires 50 and 52 work within.

In FIG. 1B, catheter 10 is shown from a side view with elongate body 26 connecting with proximal end 46 that resides outside the mammalian subject undergoing the procedure. Point 42 designates where the distal portion 26 of the elongate catheter body meets with the proximal portion 46 of the catheter. Steering unit 44 having steering knob 40 operates to apply selective tension on steering wire 50 and steering wire 52 in alternation. Both steering wires run through peripheral lumens circumferentially disposed on the exterior surface of the central working lumen 21 itself that runs through the elongate body 26. The peripheral lumens run parallel to the elongate body 26. At the steering unit 44, steering wire 50 and steering wire 52 are steered by knob 40, where turning knob 40 counterclockwise causes an articulation of the catheter tip in one direction, and turning the knob 40 clockwise causes an articulation of the catheter tip in another direction, facilitated by an internal attachment of the wire 50 and wire 52 in the steering unit 44.

A cross-sectional view of the proximal end 46 is shown in FIG. 1C wherein elongate catheter body 26 runs through catheter 10, containing wire 32 that is attached at distal attachment point 24 and proximal attachment point 30. Proximal attachment point 30 is attached to slidable unit 34 that can slide over elongate body 26, and when pulled proximally away from the distal tip 28, attached wire 32 is pulled with slidable unit 34 resulting in a uni-directional angular bend of the catheter tip 28 outside the plane of articulation of the other two wires (wires 50 and 52). In FIG. 1C attachment of the steering-wire 50 and steering wire 52 is made at attachment point 80. The tip can be bent by this mechanism any where from a slight angle, to an angle that exceeds 90 degrees.

The elongate catheter body 26 is made of material strong enough to withstand fluid and instrument access and passage, and flexible enough to articulate at the tip 28 with the steering mechanism described. Accordingly, typically, the material that makes up the catheter body 26 comprises a polymer for strength molded over and with metal wires that provide flexibility to the polymer for articulation ability and torque of the catheter. While the catheter body 26 containing the central working lumen 21 and some peripheral lumens 23 and others circumferentially disposed on an exterior surface of the central working lumen can be manufactured with any material suitable for the functional needs described, typically the elongate body can be made from a plastic or polymer composite molded over a wire weave having, for example from 8 to 24 carriers, each carrier having either single or multiple wires through the carrier. The wire can be an elastic wire, such as a wire made out of a metal or metal alloy, such as, for example, a nickel-titanium alloy, or the like. The weave can have, for example, any where from approximately 95 to approximately 140 picks per inch. The higher number of picks per inch conveys a greater flexibility of movement (and so articulation at the tip 28) to the tubular catheter body. To convey more strength, a lower number of picks/inch are used in the fabrication of the catheter body, and provides less opportunity for kinking of the elongate catheter body. The catheter body can be made so that the flexibility of the material at the tip is increased, and the durometer decreased, and also that the durometer towards the more proximal end 46 is increased, while the flexibility is decreased.

Figure 2A:
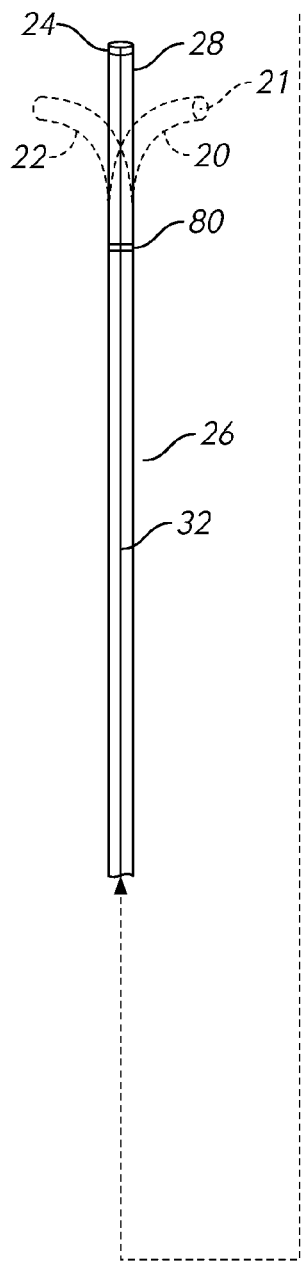
FIG. 2 depicts the elongate catheter body having a plane of articulation at the distal tip for opposed bidirectional articulation, and a rotational steering mechanism to steer opposed wires in order to provide opposed bidirectional articulation of the catheter tip.

FIG. 2 depicts the working of steering unit 44 for the bidirectional articulation of the catheter tip 28. FIG. 2A depicts attachment 24 for, attaching the central steering wire to provide its selective tension for articulation, attachment 80 for wire 50 and wire 52 distal attachment, tip 28 which is articulated in one direction 20 and an opposite direction 22, defining the plane of articulation that the two directions form, and catheter body 26 that contains the central working lumen 21 and circumferentially disposed on the exterior of that any peripheral lumens (23 and others) needed to run wires, or to provide instrument access through a peripheral lumen in addition to the access provided by the central working lumen 21.

Figure 2B:
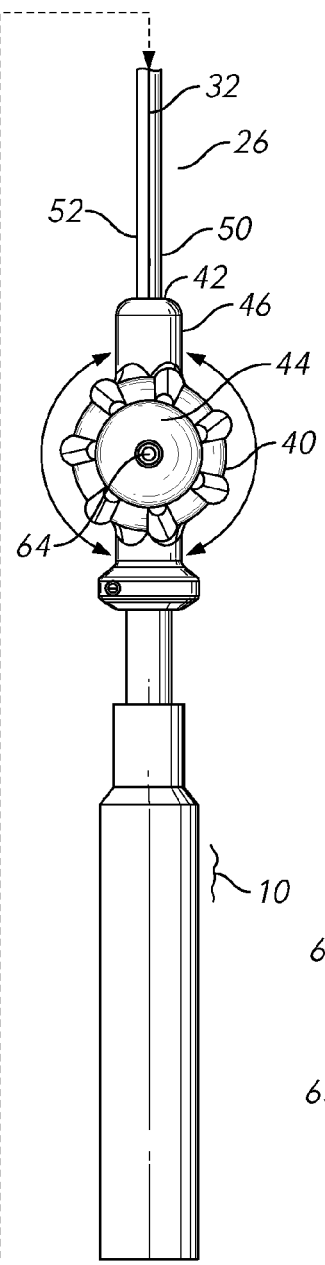

FIG. 2B depicts center point 64 of steering unit 44 having steering knob 40 that turns clockwise and counterclockwise. Point 42 delineates the separation from the portion of the catheter 26 that accesses the internal tissues of the subject mammal, and the proximal portion 46 of the device which contains the steering controls and resides outside the subject patient during the procedure.

Figure 2C:
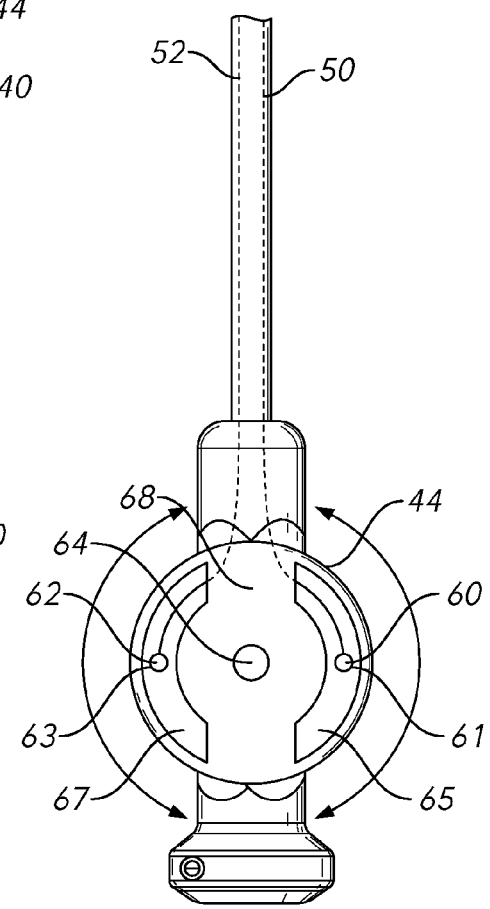

FIG. 2C depicts a cross-sectional view of the internal configuration of the steering unit 44, having an internal chamber 68 with steering wire 50 and steering wire 52 that run into the internal chamber 68 from the elongate catheter body 26 and attach at first point of proximal attachment 60 and a second point of proximal attachment 62 so that the two attachment points are in radial opposition to one another around central point 64. The attachment at points 60 and 62 can be made by any means feasible, for example, track 65 and track 67 can provide a space for movement of pin 61 and pin 63 which retain steering wire attachments 60 and 62 respectively. The pins 61 and 63 are attached to knob 40, and when knob 40 is moved counterclockwise, steering wire 52 is pulled proximally, while steering wire 50 is allowed to go slack, providing an articulation in one direction at the distal tip of the catheter from the distal attachment 80. When knob 40 is moved clockwise, steering wire 50 is pulled proximally, while steering wire 52 is allowed to go slack, providing an opposite articulation at the distal tip of the catheter from distal attachment 80.

FIG. 3 depicts possible attachment schedules for the wires in a tri-articulation. FIG. 3A shows distal attachment point 24 for attaching wire 32 that runs in a peripheral lumen 23 along the axis of elongate body 26. FIG. 3A also shows distal attachment point 80 for attaching steering wire 50 and steering wire 52. Finally, FIG. 3A depicts location 70 at which the elongate body 26 contains the central working lumen 21 and peripheral lumens such as lumen 23.

Figure 3A:
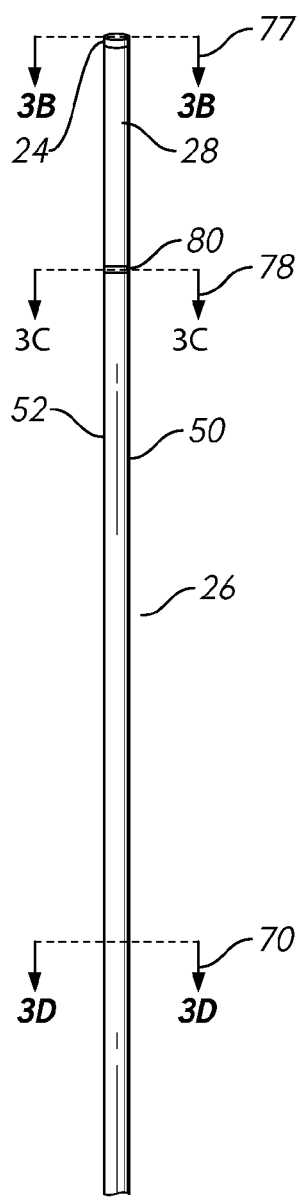
FIG. 3 depicts the elongate catheter body having a central working lumen and additionally multiple peripheral lumens for providing access to a site of procedure for such tools as a for example a scope, camera, light, suction and fluid infusion.
Figure 3B:
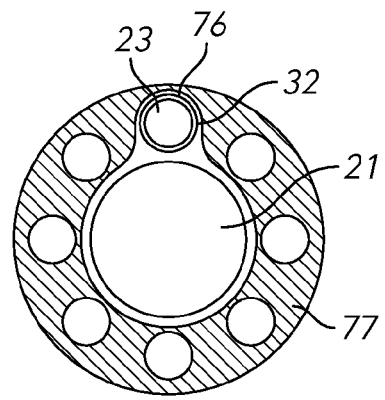
Figure 3C:
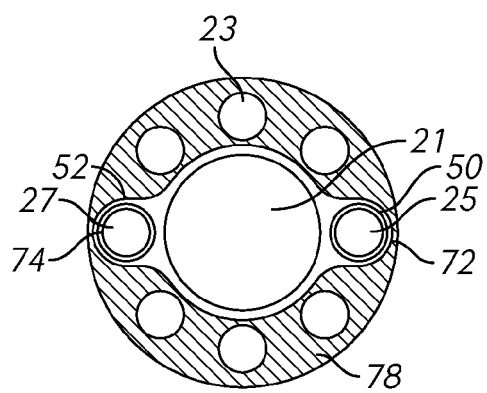

FIG. 3B depicts a cross-section 77 at attachment point 24 showing lumen 23 which carries wire 32, and location 76 at which wire 32 is distally attached. Central working lumen 21 is also depicted. FIG. 3C depicts cross section 78 at point 80 where steering wires 50 and 52 are attached at point 72 and 74 respectively. Peripheral lumen 23 carrying wire 32 is also depicted. After attaching at distal attachment point 80, peripheral lumens 25 and 27 carry steering wire 50 and steering wire 52 respectively to proximal points on the catheter body where they attach inside the steering unit 44.

Figure 3D:
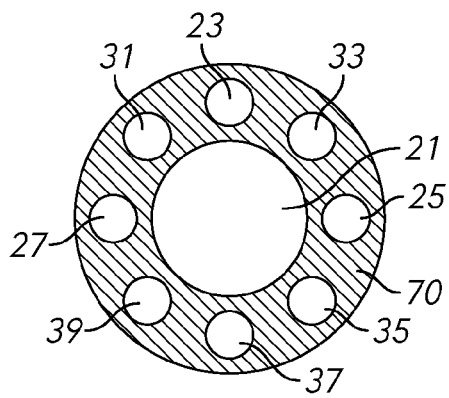

FIG. 3D depicts a proximal cross section 70 of the elongate catheter 26 having a central working lumen 21 and peripheral lumens for carrying wires 23, 25, and 27, and other peripheral lumens 31, 33, 35, 37, and 39 for access to the internal site in the mammalian subject by instruments such as for example a light, scope, camera, suction mechanism, and fluid or gas infusion mechanisms. The seals at proximal entry points for all peripheral and working lumens provide air free access by virtue of a stopper or air tight seal or valve placed at an entry point of the lumen that permits entry of the instrument but resists entry of contaminating air. The air free stopper can be a foam or spongy material, for example that seals around an entering instrument to prevent air entry as the instrument proceeds through the elongate catheter body 26. Multiple instrument air free access to the catheter can also be provided by using a branched multiple entry port at the proximal (entry) end of the catheter. Accordingly, several instruments may access the central working lumen through a multi-port branched entry, and thus share the main working lumen. When one instrument completes its procedure, it can be withdrawn to the point just clear of the main lumen, into the branching region of the multi-port entry, allowing for the next instrument to access the lumen and perform its function, and allowing also that all the accessing lumens perform their access in an air free environment.

Figure 4A:
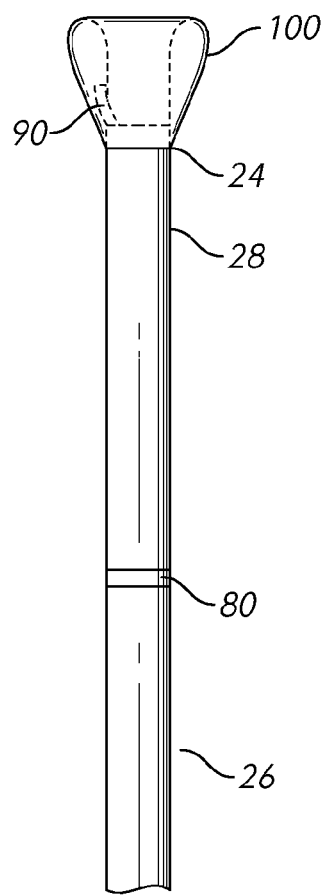
FIG. 4 depicts the distal tip of the elongate catheter having a balloon cover forming an expanded border around the central working lumen for allowing instruments, particularly visualization instruments that access the catheter and the site through the peripheral lumens, to access the site without direct contact with body fluids or tissue.
Figure 4B:
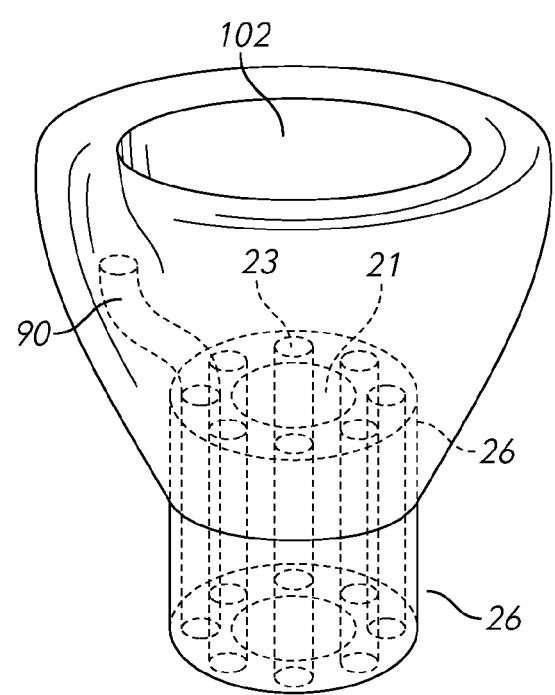

FIG. 4 depicts the donut balloon embodiment for the tip 28 of the catheter. FIG. 4A shows a side view of an expanded donut balloon 100 inflated to encase the peripheral lumens such as lumen 23, and surround an interior wall of the central working lumen 21 disposed within the elongate catheter body 26. FIG. 4A also shows hypothetical scope device 90 extending into the balloon from elongate catheter body 26 to probe the surface of the tissue or space at the site of procedure inside the subject undergoing the procedure. FIG. 4B depicts' balloon 100 in more detail, delineating opening 102 through which central working lumen 21 can provide working instrument access to tissue at the site of procedure in the mammalian subject. Within the balloon 100 peripheral lumen 23 resides and device 90 is shown hypothetically extending from catheter body 26 to perform a procedure (such as visualization) within the balloon encasement.

The tip 28 of the catheter can be made radio opaque so that the catheter tip can be visualized while it is in the body, in order to give the operator direction in articulating the movements and placement of the tip at the working site in the subject's body. Radio-opacity can be created by any means possible, including but not limited to having platinum wire at the tip, or a marker band, such as the attachment bands for the steering wires at the distal end. In addition, the polymer that makes up the tip can be doped with a radio pacifier such as, for example, barium sulfate (at a concentration of 30% or less), or tungsten loaded into the, polymer, and the like.

The attachments of the wires can be accomplished to distal and proximal points on the catheter by any means feasible, including standard means known in the art. Thus, for example, a steering wire can be soldered to a marker band at the chosen point of attachment in the catheter elongate body. Also, at the distal end where steering wire 32 is attached, the distal attachment 24 can be made by having the steering wire form a coil. The coil is then imbedded into the composite plastic or polymer material at the tip during formation of catheter body 26. Preferably, such a coil of wire is made in a reverse coil formation by being wrapped in a coil starting at the most distal portion of the catheter, and winding down proximally. At each turn, when the wire crosses itself it holds the winding wire so that the pull on the wire transmits across the distally embedded wire coil as a whole, and the wire itself is less likely to pull out of the composite plastic or polymer with force from tension coming from the proximal end.

Attachment of steering wire 50 and steering wire 52 at the proximal end 46 within the steering unit 44 can be made by soldering the wires to pin 61 and pin 63 that reside. In tracks 65 and 67 located in the internal portion 68 of the steering unit 44, where turning the steering knob 40 counterclockwise moves the 61 pin proximally in the track and applies selective tension on steering wire 50 proximally, while leaving the steering wire 52 slack, resulting in an articulation of the catheter tip in one direction. Turning the steering knob clockwise applies selective tension on steering wire 52 and moves the distal tip of the catheter to in the opposite direction as before, while making the steering wire 50 slack to permit the articulation at the tip. The steering wires 50 and 52 can be attached to the pins 61 and 63 using ball crimps on the wire or any other feasible method of attaching a wire to a pin that moves in a track, such as standard means for such attachment commonly employed in the art.

Balloon attachment to the elongate catheter is provided on an exterior surface of the elongate catheter body 26, and the balloon 100 wraps around to encase the peripheral lumens, and attaches at the inner portion of the donut configuration 102 to border the central working lumen 21, leaving the central working lumen open, but encasing the peripheral lumens. At the catheter tip such devices as a visualization device can be placed through a peripheral lumen and used to see through the balloon skin to the site of the procedure without the coordinate need to clear or clean the site of tissue or fluid that might block local visualization. Another peripheral lumen can be used to infuse air into the balloon and thereby inflate it for use. In addition, the balloon 100 can be used to provide occlusion in a lumen with fluid, for example, a vascular lumen, so that the fluid flow is stopped during the procedure.

The catheters described herein can be used for any procedure requiring a steerable catheter in a mammalian subject. Particularly the catheter is useful for minimally invasive heart surgery procedures, surgery or vascular intervention at the heart septum, procedures that involve accessing the vasculature, procedures that involve accessing a lumen and which require steering and placement of the catheter tip through that lumen, and procedures that require delicate and accurate placement of the catheter tip at the site of procedure so that instruments accessing the site have the best advantage possible to perform their designated function at the site. The catheter can also be used to deliver materials to a site inside a mammalian subject, such as therapeutic agents, drugs, or bioactive pharmaceutical agents, for example a wound healing composition, or an extracellular matrix composition. Devices or materials can be delivered through the central working lumen, for example pacemaker leads, or other device-related items. The catheter is ideal for performing minimally invasive procedures at the heart or heart valves or other organs or parts of a mammalian subject due to the tri-directional articulation of the catheter that allows careful positioning of the catheter tip at the proper site of procedure. The catheter may thus appropriately be used for minimally invasive procedures at any target organ or in any target lumen of a mammalian subject. The catheter is also designed for an ability to provide suction from the central working lumen so that the catheter tip can be secured with suction at the wall of the heart or other target organ during the procedure.

The invention also provides a catheter through which multiple instruments can access the same site. The instruments can be, for example instruments for visualization, suction, fluid infusion, gas infusion, drug delivery, suturing, stapling, and a variety of other medical tasks at the site. The instruments are accessed by sharing a common main working lumen, for example, a branched entry with multiple entry ports that resolve in the single central working lumen. The devices can be partially removed through the entry valve, then remain withdrawn from the main lumen until needed, while another device accesses the central working lumen through the same entry valve. Thus, no device is ever fully removed, but the devices can rotate their access of the central working lumen while remaining partially, but not fully withdrawn from the catheter body when not in use. Thus, an air-free catheter is maintained so that access to the site of the procedure in the subject mammal by a single catheter can provide access by multiple instruments involved in the procedure.

In one embodiment, optionally the tip 28 can have a donut balloon 100. The advantage of a balloon is that it protects the instruments from the elements at the tissue site, such as blood and fluids and debris which might get in the way of visualizing at the tip with an instrument. Other instruments that require contact with fluid or tissue can access the tissue through the central working lumen 21 formed by opening 102 of the balloon. In addition, the balloon, when inflated can provide vascular occlusion, or occlusion of any lumen that contains fluid, for the duration of the procedure.

The catheter steering mechanism unit 40 is designed to be operable with one hand if required. Turning the knob clockwise or counterclockwise provides the steering rotation, and at the same time with the same hand pulling the lever can apply selective tension on the central steering wire and move the distal tip at an angle outside the plane of articulation of the other two steering wires.

The invention provides also for methods of using the catheter. A method of depositing a composition to an interior site in a mammalian subject is provided by using the catheter to access the interior site and depositing the composition through the central working lumen of the catheter. The composition can be any prophylactic or therapeutic agent or composition considered useful for the mammalian subject, such as, for example, an extracellular matrix composition.

The invention provides a method of accessing an interior site of the mammalian subject by accessing the mammalian subject with the catheter of the invention. The invention also includes a method of placing pacemaker leads in heart tissue comprising accessing an interior site of a mammalian subject with a catheter of the invention, articulating and stabilizing the distal tip of the catheter at the heart, accessing the heart tissue through the central working lumen of the catheter with a device having a pacemaker lead at a distal end of the device, placing a lead in the heart tissue, and withdrawing the lead placement device.

The invention includes a method of facilitating a maze heart procedure comprising entering the mammalian subject with a catheter as described herein, steering the catheter to a proper position for performing the maze procedure, and performing the maze procedure on the mammalian subject. General procedures for conducting a maze procedure are standard and known in the art, e.g. as described in Khargi et al, "Surgical Treatment of atrial fibrillation: a systematic review", Eur. J. Cardiothorac. Surg. 2005 February; 27(2); 258-65; Cox J L "Surgical Treatment of Atrial Fibrillation: a review, Eurospace 2004 September; 5 Suppl. 1:S20-29; and Cox J L "Cardiac Surgery for Arrythmias" J. Cardiovasc. Electrophysiol. 2004 February; 15(2): 250-62.

The invention provides a method of performing a minimally invasive procedure to replace a heart valve comprising entering the mammalian subject with a catheter as described herein, steering the catheter to the valve to be replaced, performing the valve replacement using the catheter, and removing the catheter after the procedure is completed. Valve replacement procedures are standard in the art.

The invention also provides a method for performing a minimally invasive mitral valve repair, by accessing the site of the procedure using a catheter as described herein, and performing the mitral valve repair. Mitral valve repair procedures are standard in the art. The invention also provides a method of accessing and treating a site in a mammalian subject by steering the catheter of the invention to the site of the procedure in the mammalian subject, and performing the procedure using instruments that access the site through the central working lumen or one of the peripheral lumens of the catheter.

The invention also provides a method of making a catheter of the invention comprising providing the components of the catheter and assembling them. Although the foregoing invention has been described in detail for purposes of clarity of understanding, it will be obvious that certain modifications may be practiced within the scope of the appended claims.

We claim:

1. A catheter for accessing an interior site of a subject comprising:
   a. an elongate catheter body having a distal tip and a proximal end, a central working lumen running from the distal tip to the proximal end, first and second opposed peripheral lumens on an exterior surface of said central working lumen, said peripheral lumens in a plane of articulation relative to one another, first and second steering wires disposed through each of said first and second peripheral lumens, and a plurality of unobstructed peripheral lumens disposed circumferentially on the exterior surface of said central working lumen, said peripheral lumens being unobstructed to allow for advancement of at least one separate instrument, application of suction and fluid infusion through one of said unobstructed peripheral lumens to the interior site in the subject,
   b. an attachment at the distal tip for attaching the steering wires disposed through said peripheral lumens and
   c. a control handle coupled to both the first and second steering wires and configured to apply selective tension to the steering wires such that selective tension applied at one of the first or second steering wires causes the respective second or first steering wire to go slack to limit articulation of the distal tip in a first or second direction, said control handle located at the proximal end,
   wherein the distal tip steerable by the first and second steering wires comprises a flexible non-compressible material so that application of selective tension to the first or second steering wire causes a bend in a direction within the plane of articulation at the distal tip, said bend accomplished while a length of the elongate catheter at the distal tip along said bend resists compression of the central working lumen.

2. The catheter of claim 1, further comprising
   d. a third peripheral lumen on the exterior surface of said central working lumen having a third steering wire disposed therethrough, said third steering wire having a first attachment at the distal tip and a second attachment at the proximal end,
   e. means for applying selective tension to the third steering wire, said means located at the proximal end,
   wherein application of selective tension to the third steering wire causes a bend in a direction outside the plane of articulation of said first and second steeling wires, said bend accomplished while the length of the elongate catheter at the distal tip along said bend resists compression of the central working lumen.

3. The catheter of claim 1 or 2, wherein the flexible non-compressible material comprises a configuration selected from the group consisting of
   a. a braid angle change in braided wire embedded in composite polymer or plastic embedded running from the distal tip proximally so that the PIC count decreases proximally,
   b. a gradual diameter shift in the central working lumen running from the distal tip proximally so that the distal tip is narrow and the diameter of the lumen gradually increases proximally along the length of the elongate catheter, c. an increasing durometer of composite plastic or polymer material moving from the distal tip proximally, and d. a combination of a metal coil covered with a metal braid and embedded in composite polymer or plastic material.

4. The catheter of claim 1 or 2, wherein the control handle comprises a rotatable steering unit having a rotatable steering knob for steering the distal tip in a direction within the plane of articulation, said steering unit located at the proximal end on the catheter body outside the subject wherein said first and second wires attach to the rotatable steering knob on opposite sides of said steering knob, and further wherein turning the steering knob counterclockwise articulates the distal tip in the plane of articulation in one direction, and turning the steering knob clockwise articulates the distal tip in the plane of articulation in an opposite direction.

5. The catheter of claim 4, wherein said steering knob has an internal chamber having radially opposed circumferential tracks each comprising a pin attached to an internal surface of a rotating member of the knob, said pins slidable in their respective tracks, said first and second wires attached one on each of said opposed pins for articulating the tip in a direction in the plane of articulation when the rotating member of the knob turns clockwise or counterclockwise.

6. The catheter of claim 4 or 5, wherein said steering knob comprises a locking mechanism for locking movement of the first and second wires, whereupon release of the locking mechanism releases the steering knob to turn and steer the first or second wire and so steer or bend the catheter tip in a direction within the plane of articulation.

7. The catheter of claim 4, 5, or 6, further comprising means for adjustable friction at the steering knob so that tip deflection is maintained during a procedure.

8. The catheter of claim 2, wherein said third wire is attached at the proximal end at a slidable unit located there at, said slidable unit for providing selective tension to the third steering wire, said slidable unit able to slide along the elongate catheter in a proximal direction pulling the third wire attached at the distal tip and causing the tip to bend along the length of the elongate catheter in a direction outside the plane of articulation of said first and second peripheral lumens, said bend accomplished while the length of the elongate catheter at the distal tip along said bend resists compression of the central working lumen.

9. A catheter as in claim 1, further comprising a donut shaped balloon encasing at least one of the unobstructed peripheral lumens and forming an expanded border around an opening for the central working lumen.

10. A catheter for accessing an interior site of a subject, and for use with at least one separate instrument comprising:

a. an elongate catheter body having a distal tip and a proximal end, a central working lumen running from the distal tip to the proximal end, b. a peripheral lumen located on the exterior surface of said central working lumen having a steering wire disposed therethrough, said steering wire having a first attachment at the distal tip and a second attachment at the proximal end, and c. means for applying selective tension to the steering wire, said means located at the proximal end, wherein application of selective tension to the steering wire causes a bend in a direction of the elongate catheter, said bend accomplished while the length of the elongate catheter at the distal tip along said bend resists compression of the central working lumen, and comprising a plurality of peripheral lumens disposed circumferentially on the exterior surface of said central working lumen, said peripheral lumens being unobstructed to allow for advancement of the at least one separate instrument through one of said peripheral lumens to the interior site in the subject.

11. A catheter as in claim 10, further comprising a donut shaped balloon encasing the peripheral lumens and forming an expanded border around an opening for the central working lumen.

* * * * *